United States Patent [19]

Becker et al.

[11] Patent Number: 4,667,523

[45] Date of Patent: May 26, 1987

[54] ELECTRODE FRICTION CHUCK

[75] Inventors: David Becker, Brookline; Mark Gelo, Concord, both of Mass.

[73] Assignee: Orion Research Inc., Cambridge, Mass.

[21] Appl. No.: 837,397

[22] Filed: Mar. 7, 1986

[51] Int. Cl.⁴ ........................................... G01M 19/00
[52] U.S. Cl. .................................................... 73/866.5
[58] Field of Search ............... 73/866.5; 324/446, 447, 324/448, 449, 438, 439, 158 P; 204/197, 209, 225; 279/41 R, 46 R; 174/153 G; 248/56

[56] References Cited

U.S. PATENT DOCUMENTS

| | | | |
|---|---|---|---|
| 2,560,209 | 7/1951 | Borell et al. | 324/448 |
| 2,563,062 | 8/1951 | Perley | 324/438 |
| 3,768,115 | 10/1973 | Hoffmann et al. | 174/153 G |
| 3,837,661 | 9/1974 | Phillippi | 279/41 R |
| 4,299,363 | 11/1981 | Datschefski | 248/56 |
| 4,516,787 | 5/1985 | Venable | 279/46 R |
| 4,569,228 | 2/1986 | Bellgardt et al. | 73/866.5 |
| 4,575,947 | 3/1986 | Stauber | 33/561 |

Primary Examiner—Michael J. Tokar
Assistant Examiner—Robert R. Raevis
Attorney, Agent, or Firm—Cesari & McKenna

[57] ABSTRACT

A friction chuck for securing a test probe within a platform holder. The chuck, formed of elastomeric material, comprises a chuck body with an axially extending bore and a plurality of downward extending fingers disposed around the outer circumference of the projection of the chuck bore. Each finger has an interior bulge that extends into the projection of the chuck bore. The bulges define a segmented aperture of a diameter less than the diameter of the chuck base. When a test probe is inserted into the chuck bore it engages the fingers and bends them outwardly. There is sufficient friction between the fingers and the test probe so that the probe is secured by the fingers. The fingers have sufficient flexibility so the probe position may be changed by hand adjustment.

5 Claims, 3 Drawing Figures

ELECTRODE FRICTION CHUCK

FIELD OF THE INVENTION

This invention relates to a friction chuck for holding a test electrode and particularly to a friction chuck having fingers that can secure the electrode at any position along the length of the electrode, and can secure electrodes of varying diameter.

BACKGROUND OF THE INVENTION

Electrode holder assemblies are often seen in chemical laboratories and other locations where it is necessary to perform either qualitative or quantitative analyses on various sample solutions or substances. The assemblies are used to support one or more test probes or electrodes that are immersed in a sample of a substance in order to obtain a desired analytic test parameter from the substance. An example of such probes is a pH meter test electrode that is used to find the H+ ion concentration of a sample.

A probe holder assembly usually has a probe holder platform or bracket through which the electrode is inserted so to bring it into contact with the test samples. Typically, the platform has a mounting bore, or slot, through which the electrode is inserted. The electrode is held in the mounting bore by cap on the probe that has a diameter larger than the bore, or by a thumbscrew clamp that extends into the bore to fasten the electrode. Alternatively, the tip of the electrode rests on the bottom of the container for the test sample, in which case the platform provides only lateral support for the probe.

Each of these arrangements has disadvantages. For example, electrodes having caps that rest on the top of the holder platform are not height-adjustable. Thus, if electrodes of different heights are simultaneously used with the same supporting platform the sensor elements of the probe will be at different vertical positions. Thus one probe may rest on the bottom of the sample container, while the tip of another probe may be above the top of the sample.

Thumb screw mechanisms permit height adjustment of the probes relative to the platforms. However, they pose a breakage problem when delicate probes are used.

There are also disadvantages to having the bottom tip of the electrode rest in the sample container. For example, it would interface with the operation of a magnetic stirring bar in the bottom of the container. Most importantly, in many test electrodes the actual sensor element or membrane is located at the bottom tip of the electrode, and having that tip in contact with the bottom of the sample container will interfere with proper functioning of the electrode.

A need therefore exists for a new improved retainer for supporting a probe on a probe holder platform so that the probe can be supported in any desired position relative to the platform. The retainer should also accommodate electrodes of varied diameter, and can be easily used without posing a probe breakage problem.

SUMMARY OF THE INVENTION

The invention comprises a friction chuck composed of an elastomeric, non-conducting material, such as polyurethane, that is inserted into the mounting bore of the electrode holder platform. The chuck body is provided with a bore through which an electrode probe is inserted. Extending downward from the chuck body, beneath the electrode platform, are a plurality of fingers that extend downward and inward. The top and bottom ends of the chuck are provided with circular flanges so the chuck can be snap fitted into the electrode holder platform mounting bore.

The lower ends of the fingers define a circle of a smaller diameter than the diameter of any probe to be accommodated by the platform. Owing to the elasticity of the the chuck material, when an electrode is inserted into the chuck, the fingers bend outward and thus exert an inward force on the probe. The resulting friction force between the fingers and the probe is then sufficient to securely hold the electrode at any desired position along the length of the electrode, yet it permits easy hand adjustment of probe positions.

Also, it will be apparent that this arrangement allows a chuck to retain probes of differing diameters, so that probes can be readily interchanged for different tests.

BRIEF DESCRIPTION OF THE DRAWINGS

The foregoing and other features and advantages of the invention will be apparent from the following more particular description of the preferred embodiment of the invention, as illustrated in the accompanying drawings, in which like characters refer to the same parts throughout the different views. The drawings are not necessarily to scale, emphasis instead being placed upon illustrating the principles of invention.

DETAILED DESCRIPTION OF THE PREFERRED EMBODIMENTS

Figures 1, 2:
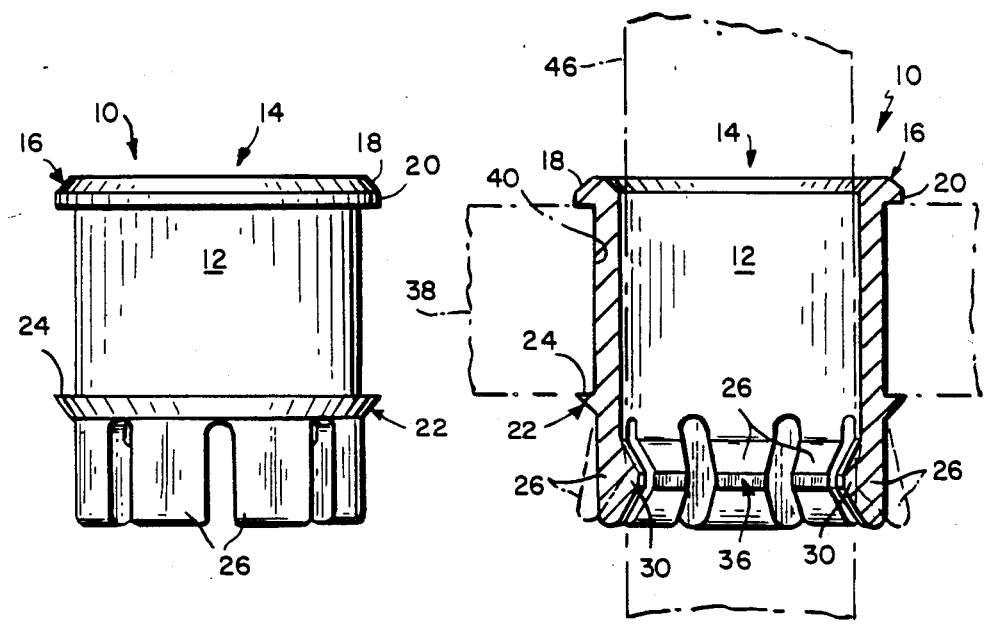
FIG. 1 is a cutaway side view of the prefered embodiment of electrode friction chuck of this invention housed in an electrode holer platform, securing an electrode.
FIG. 2 is a side view of the prefered embodiment of the electrode friction chuck of this invention.

As shown in FIG. 1, a probe friction chuck 10 of this invention is composed of elastomeric material. The chuck 10, has a tubular body 12 that is disposed in a bore 40 of a probe platform holder 38. A probe 46, extending through the bore is supported by the chuck 10.

More specifically, as shown in FIG. 2, the chuck body 12 has an upper circular flange 16 that has a beveled top surface 18 and a cylindrical side wall 20. At the bottom of the chuck body is a lower flange 22 having a triangular cross section with a top surface 24 that extends horizontally outward from the chuck body. The flanges 16 and 22 retain the chuck in the bore 42.

Figure 3:
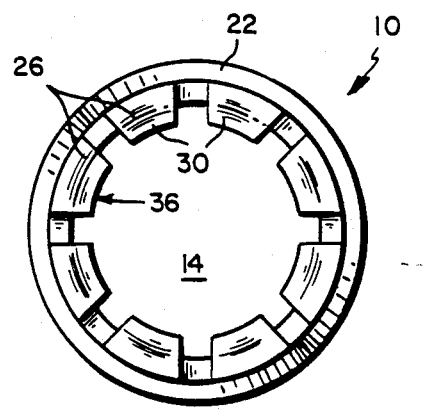
FIG. 3 is a bottom view of prefered embodiment of the electrode friction chuck of this invention.

Extending downward from the chuck body 12, from beneath the bottom flange 22, are a plurality of fingers 26. Each finger 26 has an interior bulge 30 spaced above the free end of the finger that extends into the projection of the chuck bore 14, extending through the chuck body 12 (FIGS. 1 and 3). Thus the bulges 30 define a segmented aperture 36 having a smaller diameter that that of the bore 14.

As is seen in FIG. 1, when the probe 46 is inserted into the chuck it passes freely through the bore 14. However, it has a greater diameter than the segmented aperture 36. It therefore engages the bulges 30 and bends the fingers 26 outwardly. The resilient actions of the fingers 26 combine with the relatively high coefficient of friction of the fingers to friction-secure the electrode between the fingers.

Owing to the elastomeric properties of the chuck, once the probe 46 is inserted into the aperture 36, the chuck 10 will secure the electrode at any location along the length of the electrode, yet the relative position of the probe in the platform holder 38 may be changed by simple hand adjustment.

The chuck 10 is readily displayed in the platform bore 40 by simply pushing downward into the bore. The lower flange 22 bends and compresses inwardly and then, when the illustrated position is reached, it pops out to serve as a retaining member.

What is claimed as new and desired to be secured by a Letters Patent of the United States is:

1. A chuck, for use in combination with a probe holder platform, for adjustably securing a test probe in the platform, comprising:
    (A) a tubular chuck body having top and bottom ends, a chuck bore extending axially therethrough, and upper and lower flanges for retaining said body in said platform holder; and
    (B) a plurality of elastomeric fingers extending axially away from the bottom end of said chuck body, located beneath said platform holder, and disposed around the outer circumference of the projection of said chuck bore, each of said fingers having an interior surface portion spaced above the free end of said finger that extends into the projection of said chuck bore, said interior surface portions defining a segmented aperature having a diameter smaller than the diameter of said chuck bore, whereby, when a test probe is inserted through said chuck bore, the test probe engages the interior surface portions of said fingers so as to bend said fingers outwardly so as to be friction secured by said fingers.

2. The chuck of claim 1 wherein said chuck body and said fingers are an integral unit.

3. The chuck of claim 1 wherein said fingers ae composed of polyurethane.

4. The chuck of claim 1 wherein said interior surface portions of said fingers are the outer surfaces of inwardly directed bulges integral with said fingers.

5. The chuck of claim 1 wherein one of said flanges has a triangular cross-section so the chuck can be inserted in a bore in the platform holder.

* * * * *